United States Patent [19]

Von Hasselbach

[11] Patent Number: 4,791,918

[45] Date of Patent: Dec. 20, 1988

[54] FEMORAL-NECK IMPLANT

[76] Inventor: Christoph Von Hasselbach, Armstr. 41, 4300 Essen-Borbeck, Fed. Rep. of Germany

[21] Appl. No.: 912,998

[22] Filed: Sep. 26, 1986

[30] Foreign Application Priority Data

Sep. 28, 1985 [DE] Fed. Rep. of Germany ....... 3534747

[51] Int. Cl.$^4$ ............................................. A61F 5/24
[52] U.S. Cl. ........................... 128/924 K; 128/924 V
[58] Field of Search .......... 128/924 K, 924 V, 924 Y, 128/924 P

[56] References Cited

U.S. PATENT DOCUMENTS

| 2,772,676 | 12/1956 | Pohl | 128/924 V |
| 3,489,143 | 1/1970 | Halloran | 128/924 K |
| 4,219,015 | 8/1980 | Steinemann | 128/924 P |
| 4,488,543 | 12/1984 | Tornier | 128/924 P |

FOREIGN PATENT DOCUMENTS

| 236030 | 2/1964 | Australia . | |
| 1046827 | 12/1958 | Fed. Rep. of Germany ... | 128/924 V |
| 1813807 | 6/1969 | Fed. Rep. of Germany . | |
| 2051289 | 4/1971 | Fed. Rep. of Germany ... | 128/924 K |
| 2501032 | 3/1981 | France . | |

Primary Examiner—Richard J. Apley
Assistant Examiner—David J. Isabella
Attorney, Agent, or Firm—Herbert Dubno; Andrew Wilford

[57] ABSTRACT

A femoral-neck implant has an elongated plate formed with a row of holes and adapted to fit against a femur below a trochanter, respective corticalis screws traversing the holes in the plate for securing same to the femur below the trochanter femur, a stiff upper concave portion unitary with and extending from the plate and adapted to fit against the trochanter, the portion having a plurality of holes. Respective tension-force-resisting spongiosa screws traverse the holes in the concave portion and reach from the portion into the head and through the neck of the femur. An internally threaded body is formed on the plate at a junction thereof and has a surface turned toward the femur which is flush with surfaces of the shaft and the portion turned toward the femur. The screw thread of the body has an axis which forms an obtuse angle with the plate and smooth-surfaced cylindrical shaft which extends along the axis and is provided with a male screw thread at an end of the shaft adapted to be threaded into the screw thread of the body. The cylindrical shaft is receivable slidably in a bore extending below the trochanter and into the neck and head of the femur, the tension force resistance of the spongiosa screws relieving the shaft from bending stresses.

4 Claims, 1 Drawing Sheet

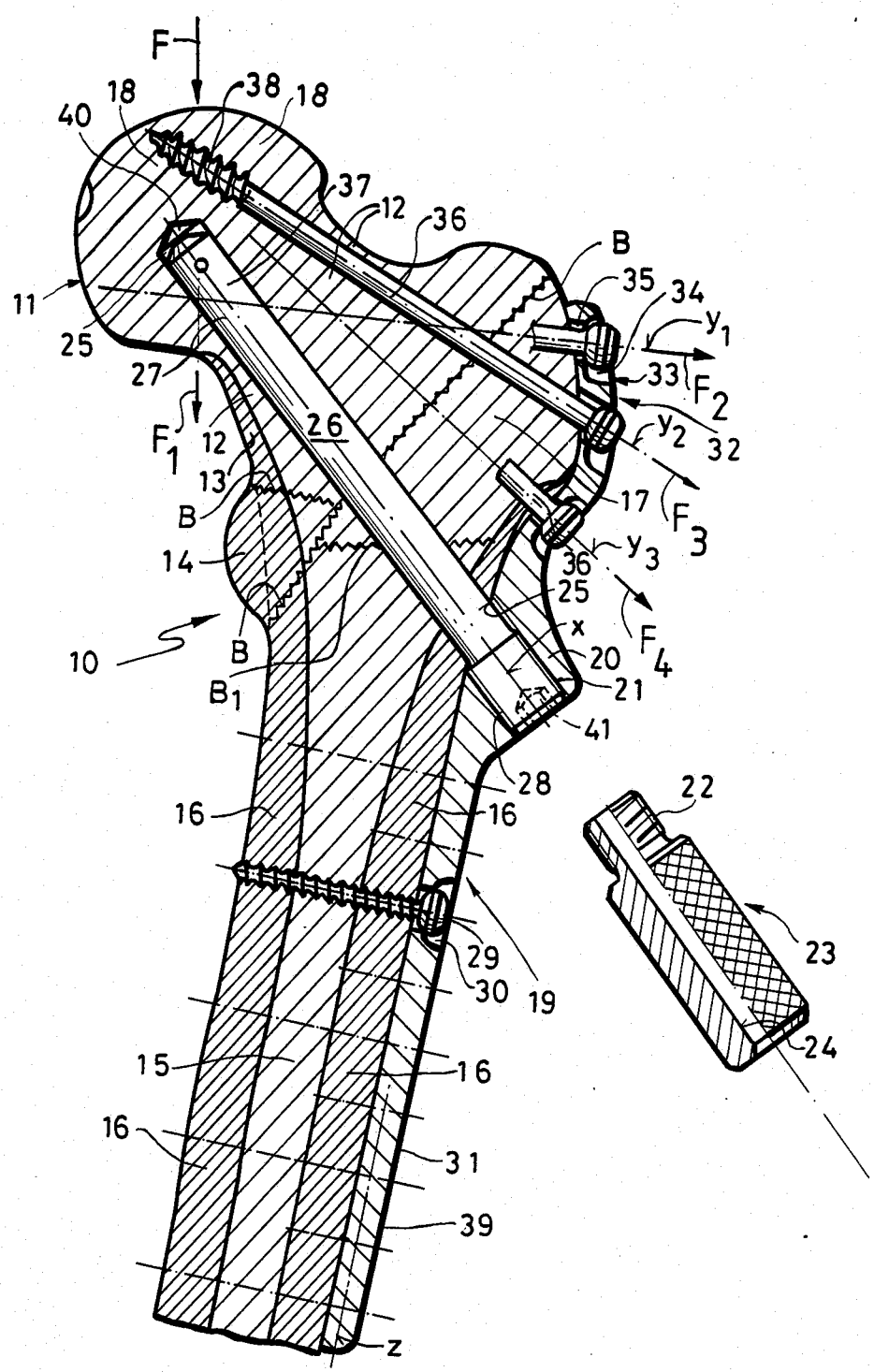

FEMORAL-NECK IMPLANT

FIELD OF THE INVENTION

The invention relates to a femoral-neck implant with a femoral-neck plate which for attachment exteriorly on the femur has along its longitudinal axis several openings for receiving corticalis screws and which is equipped at its upper end with a shaft to be implanted, extending at an obtuse angle with respect to its longitudinal axis, below the trochanter, into the femoral-neck and, if applicable, reaching into the head of the femur, and as it has become known from prior use.

BACKGROUND OF THE INVENTION

The femoral-neck plate of the previously known femoral-neck implant has a mostly U-shaped cross section. The outside of the web of the U-profile forms the outer contact surface onto the femur. In one piece with the upper end of the femoral-neck plate is the shaft, which in the known femoral-neck implant is called a blade. The blade has a U- or I-shaped cross section.

For the known femoral-neck implant the implantation process is as follows: in the case of a pertrochantery or a fracture of the femoral neck, an acceptance channel is produced manually below the trochanter with a mortising instrument adapted to the cross-sectional shape of the blade, and of suitable axial length, e.g. only into the neck of the femur, or if required into the head of the fumur. Thereafter the blade is slid into this receiving channel of bone, whereupon the femoral-neck plate is fastened exteriorily to the femur with corticalis screws.

Firstly, this known implant is unsatisfactory because the formation of the receiving channel for the blade requires much labor and time. Furthermore, during the creation of the channel, faulty angular orientation, displacement of axes, and further splintering of bones can occur.

However, the main disadvantage of the known femoral-neck implant resides in the fact that its application to unstable pertrochantery fractures, such as type Evans III and IV is indeed possible with great operative effort, but an immediate or primary postoperative load application while retaining the physiological angle of the femoral neck is impossible.

By contrast, primary postoperative loading tends to cause a mechanical collapse of the osteosynthesis previously undertaken. Since mostly elderly people who suffer unstable pertrochantery fractures must not get up for several days after the operation upon the application of the previously known implant, there exists for these patients an increased danger of complications cause by immobility, for example in form of pneumonia.

OBJECT OF THE INVENTION

Starting with the known femoral-neck implant described above, it is the object os the invention to provide an improved femoral-neck implant insertable with minimal operative effort, which while retaining the physiological angle of the femoral neck even with unstable pertrochantery fractures, permits a primary postoperative load application, without the danger of mechanical collapse of any osteosynthesis which has occurred.

SUMMARY OF THE INVENTION

This object is attained in accordance with the present invention with a femoral-neck implant in which the upper part of the femoral-neck plate forms an integrally attached extension fitted approximately to the outer contour of the greater trochanter. The extension has one or several acceptance openings for receiving screws which can be fastened pertrochantarily reaching into the femoral neck or into the head of the femur. The shaft is exteriorily smooth and circularly cylindrical, and is fastened detachably by means of a male thread at its end within a femoral acceptance thread in the upper part of the femoral-neck plate.

The property of the femoral-neck implant according to the invention can be explained as follows:

Since the shaft to be implanted below the trochanter is smooth throughout its length and is circularly cylindrical, a bore of circular cross section, easily realized with a bone drill, suffices as a reception channel inside the bone. Thereby, only as much bone substance as is absolutely necessary is removed. It is only necessary to assure that, because of possible settling of the head-neck fragment, the axial length of the bore or the receiving channel will exceed the shaft length by about 1 cm. The use of a mechanically driven bone drill for the creation of the acceptance channel has at the same time the advantage that during fabrication of the bore one can work with very small axial feed force and thus avoid displacement of individual bone fragments in the case of unstable fractures.

The spongiosa screws running pertrochantarily above the shaft are integrated into the force flow of the femoral-neck implant representing a coherent static unit therewith via the integral extension, which is resistant to bending connected to the upper portion of the femoral-neck plate.

The spongiosa screws, on the one hand, serve to pull together or to compress the bone fragments located with sliding fit on the shaft, or guided intermediately by the shaft, and on the other hand to free the shaft of harmful bending forces by taking up tension forces.

The shaft according to the invention provides a bridging osteosynthesis. As a matter of fact, there occurs a bridging of the bone fragments between the shaft-sided male thread screwed fixedly into the femoral-neck plate and the free end of the shaft. Thus the headof the femur consisting of solid spongiosa is fixed upon the free end of the shaft by at least one spongiosa screw which is in turn, at its head end, anchored n the femur-neck plate. Due to their static function, the spongiosa screws under this invention can be designated tension anchor on tension chordal screws.

The number of receiving apertures for the acceptance of the spongiosa screws in the extension can be selected at will, but normally has its practical limit as four. Depending on the fracture, it is appropriate to use at least one or at most three tension chordal screws. Thus one of the four receiving apertures can represent a reserve, to be used as need arises.

In summary, the femoral-neck implant yields the following advantages: The operational technique is simplified significantly. Extensive additional instrumentation is not necessary. The duration of the mounting operation is essentially shorter. The trauma due to the operation (destruction of soft tissue, separation of muscles) is considerably less. As a rule even for great fracture zones no additional osteosyntheses are required. With all this, the femoral-neck implant according to the invention permits primary postoperative loading and thus the earliest possible mobilization even of the elderly patient immediately after the operation. In the case of unforeseen excessively large settling, of the head-neck fragment, the invention permits replacement of the shaft, without removal of the rest of the implant, with an axially shorter shaft in a comparatively minor procedure.

The femoral-neck plate is reinforced in the area of the female thread receptacle (21).

A drill bushing with a centrally and axially oriented guide bore for the guidance of a bone drill exhibits a male thread portion and can be inserted into the female acceptance thread on the side of the femoral-neck plate.

The acceptance openings for the spongiosa screws each have a circularly cylindrical acceptance counterbore oriented away from the outside of the femoral-neck plate for the axial guidance of a drill or the shank of the spongiosa screw.

The longitudinal axis of the acceptance counterbore for the spongiosa screw immediately adjacent to the shaft runs essentially parallel to the longitudinal axis of the shaft.

The acceptance apertures or the acceptance counterbores for the spongiosa screws permit or predetermine their fan-shaped arrangement with respect to one another.

BRIEF DESCRIPTION OF THE DRAWING

The sole FIGURE of the drawing is an exploded sectional view of a femoral-neck implant according to the inventionl.

SPECIFIC DESCRIPTION

In the drawing, the upper portion of a femur 10 is shown in axial longitudinal section. The femur 10 exhibits the following main portions: the femur head 11 representing the head of a joint, the femur neck 12, Adam's arch 13, the lesser trochanter 14, the narrow space 15, the corticalis 16 and the greater trochanter 17. The greater trochanter 17 consists of a fine honeycomb-like bone substance, the spongiosa, which contrasts with the tube-like corticalis, which represents a compact bone substance. Particularly dense—and correspondingly solid—is the spongiosa in the upper portion of the femur head 11.

In the drawing, jagged lines can be seen which represent continuous fracture surfaces B, $B_1$. Thus, in the present case the entire femur head 11 including the femoral neck 12 and a considerable portion of the greater trochanter 17 is torn away; by way of aggravation, the entire lesser trochanter 14 has come off in the injury and, as a rule, is itself fractured further. Since the pertrochanteral fracture zone often represents a multiple fracture area of fragments, any residual reenforcement by bone is absent. The task is to position the bone fragments in their correct position until the fracture is healed and the femur has attained its original strength. The following measures are taken:

The bone fragments are aligned surgically, the femoral-neck plate generally designated 19 is emplaced externally on femur 10 and the entire array of aligned femur/femoral-neck plate is held in the aligned position by a suitable means, e.g. by a Vergrügge forceps.

A female thread 21 is provided in the upper portion 20 of the femoral-neck plate 19, which (portion) represents reenforcement of the material. Into said female thread 21 is threaded the male thread extension 22 of a drill bushing 23. The drill bushing 23 has a central guide bore 24 through which a bone drill of 6 mm shank diameter can be guided with relatively little bearing play. With a pilot drill not shown, a pilot hole is then made tangentially past Adam's arch all the way into the head of the femur 11. As soon as the pilot hole is made its exact position can be ascertained by means of an X-ray picture. If the position of the pilot hole is correct, then it can be drilled up in steps to a hole diameter of 6 mm. Then the drill bushing 23 is unscrewed and a bone drill of the final diameter (in the present case: 9 mm) is introduced into female thread 21 and the pilot hole is enlarged over its entire axial length. The 9 mm bone drill is self-guided within the pilot hole. Thus a receiving channel 25 of smooth cylindrical cross section throughout is produced, into which shaft 26 is then inserted. The shaft 26 consists of a solid circularly cylindrical and exteriorly smooth cylinder body 27 and a male thread formed on one end which, as shown in the dawing, is firmly screwed into female thread 21 of the femoral-neck plate 19. The longitudinally central axis of receiving channel 25 and shaft 26 is designated x.

After insertion of the shaft 26 and the pressing of the femur-neck plate 19 onto the femur, the corticalis screws 29, of which the one shown fully represents a multiplicity, are screwed into the applicable receiving aperture 30 on the side of the femur neck and through the two portions of the corticalis 16.

The longitudinal portion of the femoral-neck plate 19 arrayed below the enlarged portion 20 which receives the corticalis screws 19, is designated as the distal portion 31 of the plate. The longitudinal axis of the distal portion of the plate 31 is indicated by dot-and-dash line z. The longitudinal axis includes an obtuse angle with the central longitudinal axis x of the shaft 26. In adaptation to the prevailing individual anatomy, this obtuse angle can be chosen between 130° and 100°, and standardized upon at manufacture. The axial length of the distal plate portion is in principle also variable, in order to be able to include fractures into the osteosynthesis which extend further subtrochantarily.

The shaft 26 extending tangentially along Adam's arch 13 is located below the greater trochanter 17. An axial excess of the bore 25 beyond the free end of shaft 26 is designated 40.

Above the thickened upper end portion 20 of the femoral neck plate 17, an extension generally designated 32 continues the plate and has a shape approximately adapted to the outer outline of the greater trochanter 17.

The extension 32 has up to four receiving openings 33, each of which posseses a concave screw head receptacle 34, and extending therefrom, a continuing circularly cylindrical centering receiving opening 35.

The receiving opening 33 can also be made without the centering receiving openings, so that a spatially orientable positioning of the drill is possible within limits.

Via and through the receiving openings, 33 holes are produced which intersect the greater trochanter 17 and reach into the relatively solid spongiosa of the femur head 11. Into these holes spongiosa screws 36 are inserted, of which in the drawing only one is showhn in its entirety. Of the other spongiosa screws 36, partially not shown, only their central longitudinal axes and their head areas can be seen in the drawing. The central longitudinal axes of the spongiosa screws 36 are designated $y_1$, $y_2$ and $y_3$. The spongiosa screw corresponding to central longitudinal axis $y_3$ runs in vicinity of shaft 26 and should, if at all possible, deviating from the drawing, be arrayed essentially parallel to the longitudinal axis x of shaft 26.

The spongiosa screw 36 with the central longitudinal axis $y_3$ draws the bone fragments together and thus assures close fit in the area of the fracture zones. However, the lesser trochanter 14, previously detached, is held in a wire cerclage, not shown, if necessary. When all the elements 26, 29, 36 have assumed their final positions, the following static conditions result: The hip force acting on femur 10 on the joint side is generally designated F. This hip force is divided vectorially, so that shaft 26 transmits the force component $F_1$ which is substantially smaller than the hip force F. The considerable difference between F and $F_1$ is taken up by tension forces $F_2$, $F_3$ and $F_4$, which act along the central longitudinal axes $y_1$, $y_2$ and $y_3$ of the spongiosa screws 36 which are to be considered as tension achors or tension chord screws, respectively.

It is also important that the hip force F must be taken up by shaft 26 in a much smaller fraction as the force $F_1$, while avoiding harmful loading in bending. The remaining force components however are taken up by the tension chord screws 36 and carried into the femoral-neck plate 19 which is stiff overall as regards shape. On the side of the femur, the closing of the force train occurs thereby between the free end portion 37 of the shaft 26 and the free end portions 38 of the spongiosa screws 36 via the relatively strong, dense spongiosa in the upper portion of the femur head 11.

The takeup of the forces outlined above is further improved by the fact that the central longitudinal axes $y_1$, $y_2$ and $y_3$ and thus the three spongiosa screws 36 are arrayed in fan shape. Particularly through this arrangement there results the great torsional strength of the osteosynthesis represented.

The outer portion of the femur neck plate 19 is designated 39. For the screw actuation of shaft 26 an interior hexagon socket 41 is provided.

All implant components consist of implant steel, titanium, or other metallic or non-metallic material.

I claim:

1. A femoral-neck implant comprising:
an elongated plate formed with a row of holes and adapted to fit against a femur below a trochanter thereof;
respective corticalis screws traversing said holes in said plate and securing said plate to the femur below the trochanter;
a stiff upper concave portion unitary with and extending from said plate and adapted to fit generally complementarily over said trochanter, said portion having three holes;
respective tension-force-resisting spongiosa screws arrayed nonparallel to one another in a fanlike array, traversing said holes in said concave portion, and reaching from said portion into the head and through the neck to the femur to secure the portion to the trochanter;
an internally threaded body formed on said plate at a junction thereof with said portion, having a surface turned toward the femur which is flush with surfaces of the femur and of said portion turned toward said femur, the spongiosa screw of the hole closest to the shaft being generally parallel thereto and the other spongiosa screws being at increasingly large angles with the shaft with the spongiosa screw of the hole furthest from the shaft crossing and lying next to the shaft in the trochanter, the screw thread of said body having an axis forming an obtuse angle with said plate; and
a smooth-surfaced cylndrical shaft extending along said axis generally below the fanlike array of spongiosa screws and having a lower end porvided with a male screw thread adapted to be threaded into the screw thread of said body, said cylindrical shaft being receivable slidably in a bore extending below said trochanter and into the neck and head of the femur, the tension force resistance of said spongiosa screws relating said shaft from bending stresses.

2. The femoral-neck implant defined in claim 1, further comprising a drill guide, having a centrally and axially oriented guide bore for guiding a bone drill along said axis and having a male thread receivable in said internal thread of said body.

3. The femoral-neck implant defined in claim 1 wherein said holes in said portion have circular cylindrical passages for guiding a drill and shanks of said spongiosa screws.

4. The femoral-neck implant defined in claim 3 wherein said passages are mutually oriented to define the fanlike array for said spongiosa screws.

* * * * *